United States Patent
Castillo (10) Patent No.: US 9,675,493 B2
(45) Date of Patent: Jun. 13, 2017

(54) GOGGLE BREATHING SYSTEM

(71) Applicant: James D. Castillo, Los Alamos, CA (US)

(72) Inventor: James D. Castillo, Los Alamos, CA (US)

( * ) Notice: Subject to any disclaimer, the term of this patent is extended or adjusted under 35 U.S.C. 154(b) by 237 days.

(21) Appl. No.: 14/502,348

(22) Filed: Sep. 30, 2014

(65) Prior Publication Data

US 2015/0173933 A1 Jun. 25, 2015

Related U.S. Application Data (60) Provisional application No. 61/918,826, filed on Dec. 20, 2013, provisional application No. 61/937,018, filed on Feb. 7, 2014.

(51) Int. Cl.
*A61F 5/08* (2006.01)
*A61F 9/02* (2006.01)

(52) U.S. Cl.
CPC ............... *A61F 5/08* (2013.01); *A61F 9/026* (2013.01); *A61F 9/029* (2013.01)

(58) Field of Classification Search
CPC .. A61F 5/08; A61F 9/026; A61F 9/029; A61F 9/028
USPC ............. 351/136, 138, 158; 606/201–204.55
See application file for complete search history.

(56) References Cited

U.S. PATENT DOCUMENTS

| | | | |
|---|---|---|---|
| 3,835,848 A | 9/1974 | Berner | |
| 5,533,503 A | 7/1996 | Doubek et al. | |
| 5,913,873 A | 6/1999 | Blach et al. | |
| 6,006,746 A | 12/1999 | Karell | |
| 6,033,422 A | 3/2000 | Blach et al. | |
| 6,352,548 B1 | 3/2002 | Blach et al. | |
| 6,533,412 B1 | 3/2003 | Wang et al. | |
| 6,676,681 B1 | 1/2004 | Blach et al. | |
| 6,823,864 B2 | 11/2004 | Blach et al. | |
| 7,091,634 B2 | 8/2006 | Yi et al. | |
| D639,762 S | 6/2011 | Brogden et al. | |
| D644,324 S | 8/2011 | Brunner et al. | |
| D644,325 S | 8/2011 | Brunner et al. | |
| 8,042,542 B2 | 10/2011 | Ging et al. | |
| D696,400 S | 12/2013 | Brogden et al. | |
| D701,957 S | 4/2014 | Brunner et al. | |
| D703,318 S | 4/2014 | Brunner et al. | |
| 2007/0105824 A1 | 5/2007 | Erickson-Miller et al. | |
| 2008/0097517 A1 | 4/2008 | Holmes et al. | |
| 2009/0188023 A1 | 7/2009 | Hsu | |

(Continued)

OTHER PUBLICATIONS

International Search Report and Written Opinion for International Application No. PCT/US14/69817, Mar. 11, 2015, 11 pages.

*Primary Examiner* — Todd J Scherbel
*Assistant Examiner* — Son Dang
(74) *Attorney, Agent, or Firm* — Stetina Brunda Garred and Brucker (57) ABSTRACT

Provided is a goggle kit including a goggle clip attachable to the goggle frame, and a corresponding nose element, which adheres to the user's nose. The nose element and the goggle clip are configured to be detachably engageable therewith, such that when the nose element is placed on the user's nose and the goggle is placed over the user's eyes, the goggle clip and nose element may be engaged with each other, thereby urging the nasal opening of the user to dilate.

20 Claims, 7 Drawing Sheets

(56) References Cited

U.S. PATENT DOCUMENTS

2010/0309425 A1* 12/2010 Zelazowski .............. G02C 1/08
                                                     351/138
2011/0000483 A1    1/2011 Matthias et al.
2012/0036607 A1    2/2012 Beliveau
2012/0172923 A1    7/2012 Fenton et al.

* cited by examiner

GOGGLE BREATHING SYSTEM

CROSS-REFERENCE TO RELATED APPLICATIONS

This application claims the benefit of U.S. Provisional Application No. 61/918,826, filed Dec. 20, 2013, and U.S. Provisional Application No. 61/937,018, filed Feb. 7, 2014, the contents of which are expressly incorporated herein by reference.

STATEMENT RE: FEDERALLY SPONSORED RESEARCH/DEVELOPMENT

Not Applicable

BACKGROUND OF THE INVENTION

1. Field of the Invention

The present invention relates generally to an eyewear accessory kit, and more specifically to an eyewear accessory kit designed to enhance nasal airflow for the wearer by urging the wearer's nostrils to a more open position.

2. Description of the Related Art

It is readily understood that breathing is important when playing sports or taking part in physical competition due to the increased demand for oxygen by the body. Breathing may be achieved by drawing air into the body through an individual's nostrils and/or through the individual's mouth. However, in some instances, it is preferable to breathe almost exclusively through the nostrils, as there may be a downside to breathing through one's mouth. Along these lines, breathing through the mouth may lead to rapid water loss and heat loss, both of which increase the likelihood of exercise-induced asthma.

It is also understood that eyewear is commonly used when participating in many sports and activities. Such eyewear may include protective eyewear, or vision-enhancing (e.g., prescription) eyewear. For instance, goggles are readily worn by many athletes participating in snowboarding, skiing, motocross, automotive racing, basketball, baseball, hockey, etc. Goggles are typically configured such that a portion of the goggle frame extends over the wearer's nose, and thus, goggles may impact one's ability to breathe through the wearer's nasal passage.

Moreover, many goggles are fitted with a foam liner which interfaces with the wearer's face to create a barrier or seal which prevents snow, rain, dirt or other debris from entering the goggles and creating a potential irritant in the wearer's eye. In order to create an effective seal or barrier around the goggles, the goggles are compressed against the wearer's face, typically through the use of an elastic band which is worn around the head. The compression of the foam liner against the wearer tends to compress the nasal passages of the wearer, which further inhibits the ability of the wearer to breathe through the nose.

Accordingly, there is a need in the art for a device which can be used with a goggle or other eyewear for enhancing the wearer's ability to breathe through the wearer's nasal passage. Various aspects of the present invention address this particular need, as will be discussed in more detail below.

BRIEF SUMMARY OF THE INVENTION

In accordance with one embodiment of the present invention, there is provided a goggle kit including a goggle clip attachable to the goggle frame, and a corresponding nose element, which adheres to the wearer's nose. The goggle clip attaches to the goggle frame to compress the foam liner to create space for the nose element to enable the nose element to move outward toward the clip. The nose element and the goggle clip are configured to be attachable to each other, such that the nose element is moved in an outward direction and/or forward direction to engage with the clip. The outward and/or forward movement of the nose element causes the nasal opening of the wearer to dilate. Therefore, even though the wearer is using goggles, the wearer can breathe more freely through his or her nasal passageway.

The goggle clip may include a pair of clip tabs which are transitional between an extended position and a clamping position for securing the goggle clip to the goggle frame. The clip tabs may move toward each other as the clip transitions from the extended position toward the clamping position. The goggle clip may include a spring clip, or may include a hinge to allow the clip to transition between the extended and clamping positions.

The nose element may include a pair of nose pieces positionable over respective ones of the user's nostrils. The nose element may also include a single strip which is extendable over the user's nose between the user's nostrils. The nose element may include an adhesive for temporarily securing the nose element to the user.

Engagement between the goggle clip and the nose element may be by way of magnetic attraction, hook and loop fasteners (e.g., VELCRO), adhesives, snaps, clips, friction, or other mechanical engagement mechanisms known in the art.

According to one embodiment, there is provided an eyewear system adapted to open a nasal passage of a user. The eyewear system includes a wearable frame having a bridge section configured to be placeable adjacent the nose of the user. A nasal attachment member is configured to be selectively placeable on the nose of the user adjacent the nasal passage. The nasal attachment member is adapted to be urged toward the wearable frame in response to placement of the wearable frame adjacent the nose of the user to cause the nasal passage of the user to open.

The system may include a liner coupled to the wearable frame and configured to interface with the user when the wearable frame is placed on the user. The liner may be formed from a compressible material. The system may additionally include a clip configured to be selectively attachable to the wearable frame and adapted to urge the nasal attachment member toward the wearable frame in response to placement of the wearable frame adjacent the nose of the user. A peripheral barrier member may be coupled to the clip and configured to interface with the user to mitigate the passage of particulate between the wearable frame and the user when the clip is attached to the wearable frame and the wearable frame is placed adjacent the nose of the user.

The clip may include a first clip member and a second clip member pivotally coupled to the first clip member. The first clip member may be pivotable relative to the second clip member between an open position and a closed position. An angle between the first and second clip members may decrease as the first and second clip members pivot from the open position toward the closed position. The first and second clip members may be configured to become locked when the first and second slip members are in the closed position.

The nasal attachment member may be configured to be magnetically urged toward the wearable frame. The system may include a frame magnet coupled to the wearable frame and magnetically attractable to the nasal attachment member.

According to another embodiment, there is provided a method of enhancing a nasal airway of a user wearing goggles having a compressible barrier member. The method includes compressing the compressible barrier member on the goggles to form a recess within the barrier member, attaching a nasal attachment member to the user adjacent the user's nostrils, and placing the goggles on the wearer after the compressible barrier member has been compressed, placement of the goggles on the wearer urges the nasal attachment member to move into the recess formed within the barrier member, movement of the nasal attachment member into the recess causes the nasal airway of the user to dilate.

The present invention will be best understood by reference to the following detailed description when read in conjunction with the accompanying drawings.

BRIEF DESCRIPTION OF THE DRAWINGS

These and other features and advantages of the various embodiments disclosed herein will be better understood with respect to the following description and drawings, in which.

Common reference numerals are used throughout the drawings and the detailed description to indicate the same elements.

DETAILED DESCRIPTION OF THE INVENTION

The detailed description set forth below in connection with the appended drawings is intended as a description of certain embodiments of a goggle breathing system and is not intended to represent the only forms that may be developed or utilized. The description sets forth the various structure and/or functions in connection with the illustrated embodiments, but it is to be understood, however, that the same or equivalent structure and/or functions may be accomplished by different embodiments that are also intended to be encompassed within the scope of the present disclosure. It is further understood that the use of relational terms such as first and second, and the like are used solely to distinguish one entity from another without necessarily requiring or implying any actual such relationship or order between such entities.

Referring now to the drawings, wherein the showings are for purposes of illustrating a preferred embodiment of the present invention only, and are not for purposes of limiting the same, there is depicted a system 10 configured to open or dilate the nasal passages 12 of an individual 14 wearing eyewear, such a goggles 16. The system 10 generally includes a nasal attachment member 15 including a pair of nasal elements 17 which are worn by the wearer 14 adjacent the wearer's nostrils. The system 10 is configured such that when the goggles 16 are placed on the wearer 14, the nasal attachment member 15 is urged toward the goggle frame 20, which results in dilation of the nasal opening, thereby making it easier for the wearer 14 to breathe, despite the existence of the goggles 16 extending over the wearer's nose 18.

Figure 1:
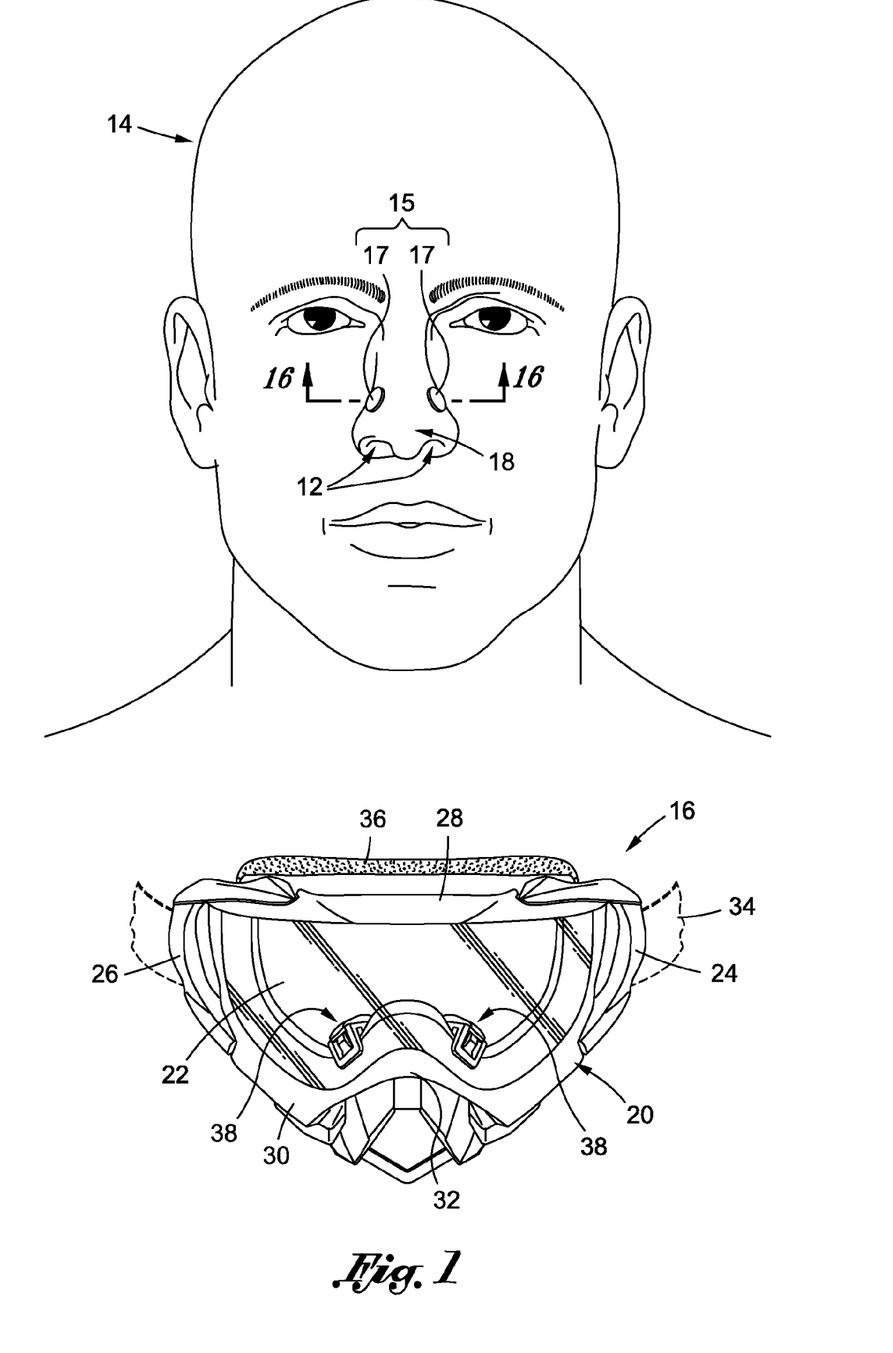
FIG. 1 is a front view of a user wearing a pair of nasal elements and goggles having clips attached thereto which cooperate with the nasal elements to open the nasal passage.

Referring now specifically to FIG. 1, there is depicted a set of goggles 16 having a wearable frame 20 including a frame opening, within which is positioned a lens 22. The frame 20 includes opposed lateral end portions 24, 26, a top portion 28, and an opposing bottom portion 30 having a bridge section 32 which fits over the nose 18 of the wearer 14. The frame 20 may be fabricated from plastic, rubber, or other materials known by those skilled in the art. A headband or strap 34 may be connected to the opposed lateral end portions 24, 26 of the frame 20 for securing the frame 20 to the wearer's head.

Although the exemplary embodiment shows the wearable frame 20 as being a frame for goggles 16, it is understood that the term wearable frame may broadly refer to other frames which may be worn by a wearer, such as frames associated with various helmet systems and the like.

A foam liner 36 extends around an inner peripheral portion of the frame 20 and rests against the wearer's head when the goggles 16 are worn by the wearer 14. The foam liner 36 is designed to interface with the wearer's face to create a seal or barrier around the frame 20 so as to prevent unwanted debris or particulate from passing between the goggles 16 and the wearer 14 so as to protect the wearer's eyes. The liner 36 is preferably formed of a breathable material so as to allow air to pass therethrough to allow for ventilation within the goggles 16.

It is understood that goggles 16 come in various shapes, sizes and configurations depending on the particular size of the wearer 14, as well as the intended use of the goggles 16. Consequently, the term "goggles" refers broadly to any eyewear that is worn while snowboarding, snow skiing, motorcycle racing (e.g. motocross), automobile racing, or playing a wide variety of sports such as basketball, baseball, football, hockey, etc., for the purpose of protecting the wearer's eyes, or for providing enhanced visibility.

One embodiment of system 10 additionally includes a goggle attachment member or clip(s) 38, which may be selectively and securely attached to the frame 20 of the goggle 16. Each clip 38 is specifically adapted to engage with a corresponding nasal element 17 through complimentary fastening members. The engagement between the clip 38 and the nasal element 17 causes dilation of the nasal passageways, as will be described in more detail below. When the clip 38 is attached to the goggle 16, the clip 38 compresses the liner 36 to create space around the wearer's nose 18 to allow the nasal element 17 to be drawn outwardly and forwardly thereby causing the nose 18 to dilate.

According to one embodiment, and referring now specifically to FIGS. 2-8, a first embodiment of a clip 38 is shown, which includes a first clip member 42 and a second clip member 44 pivotally connected to the first clip member 42 via a hinge 45. The first and second clip members 42, 44 form opposing locking tabs defining a clip channel 46 (see FIG. 7) therebetween sized and adapted to receive a portion of the goggle frame 20 to allow the clip 38 to clamp onto the goggle frame 20.

As shown in FIGS. 3-8, the first clip member 42 includes a pair of opposing lateral arms 48, 50 which are interconnected by a connecting arm 52. The opposing lateral arms 48, 50 and the connecting arm 52 collectively define a first clamping surface 54 (see FIG. 7), which faces the clip channel 46. The first clip member 42 further includes a locking arm 56 extending from the connecting arm 52, wherein the locking arm 56 includes a first locking surface 58 (see FIG. 3), a second locking surface 60, and an outer cam surface 61, the purposes of which will be described in more detail below.

The second clip member 44 includes a primary wall 62 having a second clamping surface 64 facing the clip channel 46 in opposed relation to the first clamping surface 54 of the first clip member 42. The first and second clamping surfaces 54, 64 define an angle $\Theta$ (see FIG. 7) therebetween. The second clip member 44 further includes an outer surface 65 (see FIG. 7) opposite the second clamping surface 64. A secondary wall 66 extends from the primary wall 62 and includes a pair of lateral arms 63, 67, and a distal arm 69 extending between the lateral arms 63, 67. An opening 68 is formed within the secondary wall 66, wherein the opening 68 is sized and adapted to receive the locking arm 56 of the first clip member 42.

Figure 7:
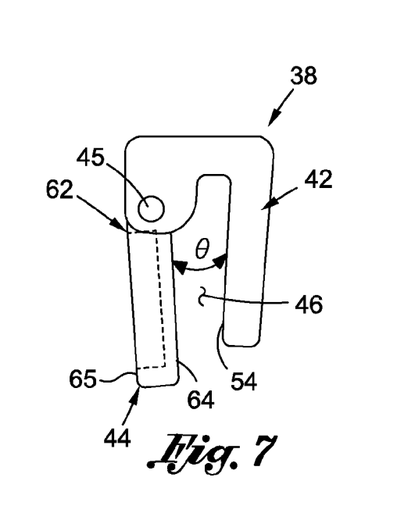
FIG. 7 is a side view of the clip shown in FIG. 3, wherein the clip is in the closed position.
Figure 8:
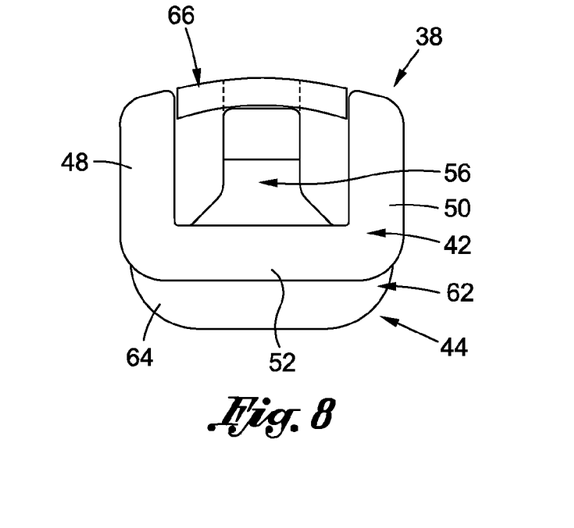
FIG. 8 is a rear view of the clip shown in FIG. 3, wherein the clip is in the closed position.
Figure 9:
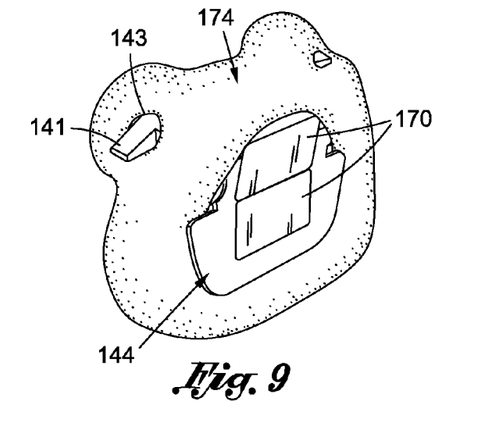
FIG. 9 is a front upper perspective view of a second embodiment of a clip having a foam liner and a pair of magnets.
Figure 10:
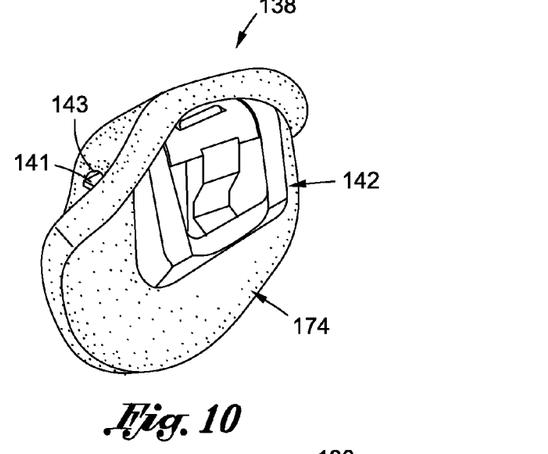
FIG. 10 is a rear upper perspective view of the clip shown in FIG. 9, wherein an end portion of the foam liner has been moved relative to its position shown in FIG. 9.
Figure 11:
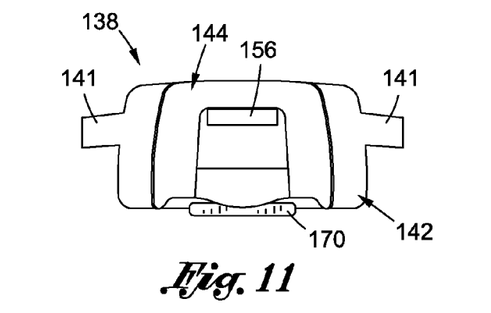
FIG. 11 is a top view of the clip shown in FIG. 9.
Figure 12:
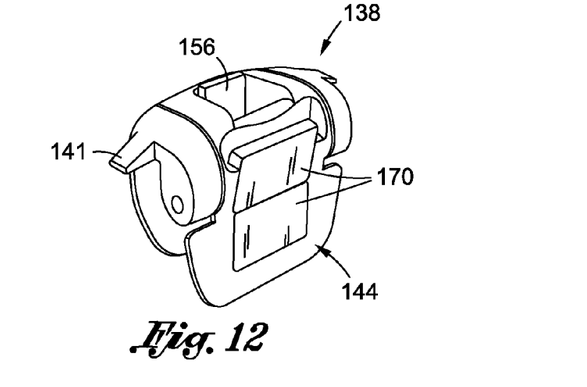
FIG. 12 is an upper perspective view of the clip depicted in FIG. 9.
Figure 13:
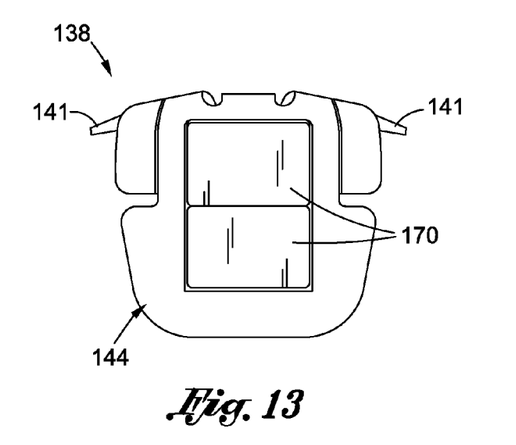
FIG. 13 is a front view of the clip depicted in FIG. 9.
Figure 14:
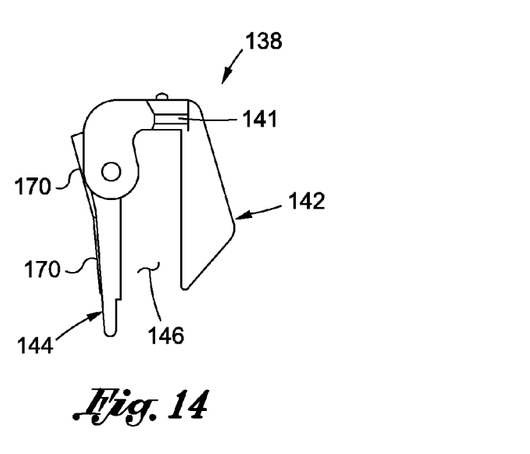
FIG. 14 is a side view of the clip depicted in FIG. 9.

The first clip member 42 is adapted to be selectively transitional relative to the second clip member 44 between an open position and a closed position. In particular, the angle $\Theta$ between the first clamping surface 54 and the second clamping surface 64 decreases when the first and second clip members 42, 44 transition from the open position toward the closed position. Conversely, the angle $\Theta$ between the first clamping surface 54 and the second clamping surface 64 increases when the first and second clip members 42, 44 transition from the closed position toward the open position.

When the clip 38 is in the open position (see FIG. 3), the locking arm 56 of the first clip member 42 extends through the opening 68 formed in the secondary wall 66 of the second clip member 44. Furthermore, the distal arm 69 rests against the outer cam surface 61, which prevents the clip 38 from freely moving from the open position toward the closed position. For the clip 38 to be transitioned from the open position toward the closed position, the user presses the first clip member 42 toward the second clip member 44. This causes the locking arm 56 to flex, which in turn, allows the distal arm 69 to move along the locking arm 56 toward the locking surfaces 58, 60, and the locking arm 56 to retract through the opening 68 until a portion of the secondary wall 66 interfaces with the first and second locking surfaces 58, 60 of the locking arm 56. Once the clip 38 is in the closed position, the engagement between the secondary wall 66 and the locking arm 56, specifically, the second locking surface 60, prevents the clip 38 from moving from the closed position toward the open position. Therefore, the clip 38 may be adapted to prevent free movement between the open position and the closed position.

In order to move the clip 38 from the closed position toward the open position, the locking arm 56 is disengaged from the secondary wall 66, typically by pressing the locking arm 56 toward the primary wall 62 of the second clip member 44 until the locking arm 56 can be advanced through the opening 68. In this respect, the first clip member 42 is constructed from a material having suitable flexibility to enable flexing of the locking arm 56 relative to the connecting arm 52.

One or more magnets 70 is connected to the clip 38 at an engagement region of the clip 38. The magnet 70 is nested within a cavity extending into the clip 38 from the outer surface 65. The magnet 70 and the cavity within which the magnet 70 is nested are preferably configured such that the outer surface of the magnet 70 is substantially flush with the outer surface 65 of the second clip member 44 when the magnet 70 is nested within the cavity. The magnet 70 is adapted to magnetically urge the nasal attachment member 15 worn by the wearer 14 toward the goggle frame 20 for purposes of opening or dilating the nasal passages of the wearer 14.

According to one embodiment, the magnet 70 is a neodymium, N42 grade magnet, although magnets of differing grades or materials may also be used without departing from the spirit and scope of the present invention. Furthermore, the size of the magnet 70 may range from approximately 0.25"-0.75" in diameter. For instance, the magnet 70 may be ⅜" or ½" in diameter, although other sizes may also be used.

When the clip 38 is placed on the goggle frame 20, the clip 38 compresses the foam 36 lining the inner perimeter of the goggle 16 to create a cavity. This cavity creates space within the liner 36 adjacent the wearer's nostril to allow the nasal element 17 to move outwardly causing the nostril to dilate. However, compressing the foam 36 on the goggle 16 may compromise the seal or barrier around the goggle 16 and allow rain, snow, dirt or other particulate to enter the goggle 16 and interfere with the wearer's 14 vision. Therefore, according to one embodiment, and referring now to FIGS. 2 and 2A, a peripheral foam liner 74 is coupled to the clip 38 and operates as a peripheral barrier member around the clip 38 by extending between the clip 38 and the foam 36 on the goggle 16. The clip liner 74 and goggle liner 36 cooperate with each other to prevent particulate from entering the goggles 16, even though the clip 38 has compressed the foam 36 on the goggle 16. Furthermore, the foam-against-foam arrangement between the clip liner 74 and goggle liner 36 adds to grip between the clip 38 and the goggle 16. The peripheral foam liner 74 is preferably configured to enable air to pass therethrough to allow for ventilation.

Figure 2:
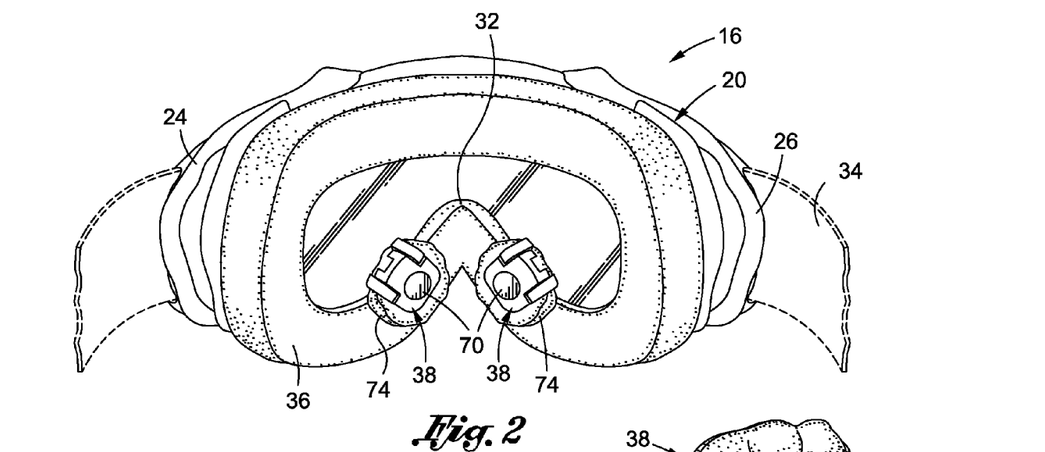
FIG. 2 is rear perspective view of the goggles and clips depicted in FIG. 1.
Figures 2A, 3, 4:
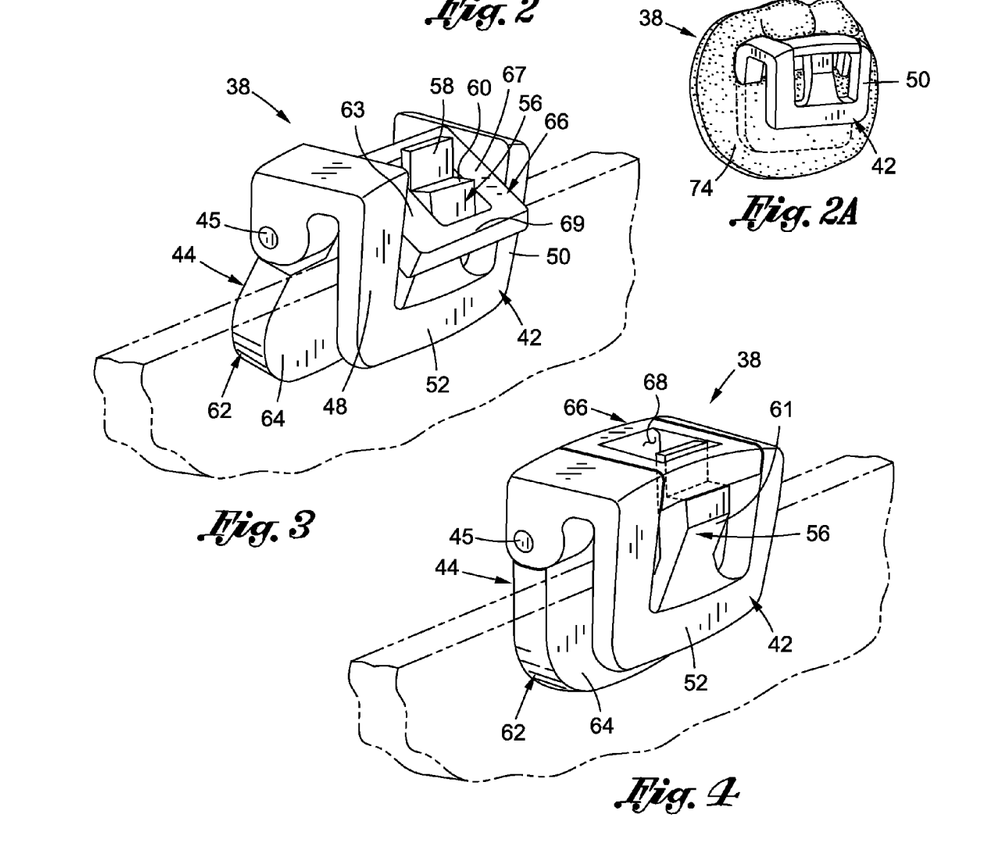
FIG. 2A is an upper perspective view of the clip shown in FIG. 2 having a barrier member attached thereto.
FIG. 3 is a perspective view of the clip shown in FIG. 2 with the foam liner removed, wherein the clip is in an open position.
FIG. 4 is a perspective view of the clip shown in FIG. 3, wherein the clip is in the closed position.
Figure 5:
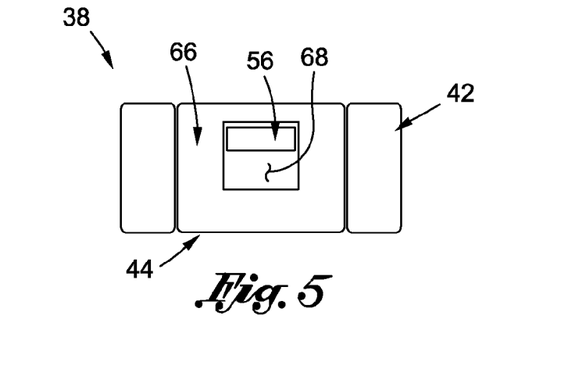
FIG. 5 is a top view of the clip shown in FIG. 3, wherein the clip is in the closed position.
Figure 6:
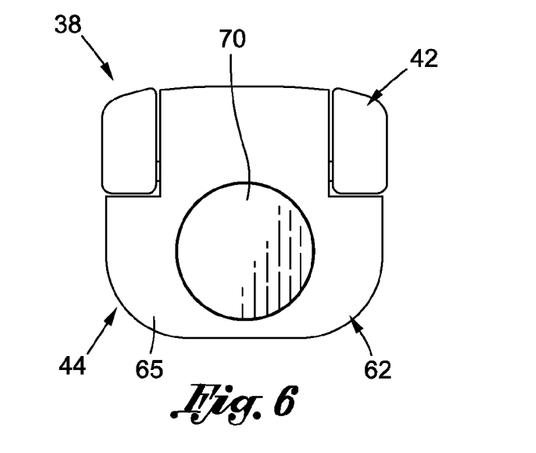
FIG. 6 is a front view of the clip shown in FIG. 3, wherein the clip is in the closed position.

FIG. 2 shows two clips 38 attached to the goggle 16 in spaced relation to each other, wherein each clip 38 includes its own peripheral foam liner 74. In another embodiment, the pair of clips 38 includes a common foam liner (not shown) which includes a bridge section that extends over the nose. When the pair of clips 38 having a common foam liner is used, it causes the goggle 16 to set slightly farther from the nose, creating more of a gap, which increases the space between the magnetic member and the user's nose allowing for greater dilation of the nose.

Referring now specifically to FIGS. 9-14, there is depicted a second embodiment of a clip 138. The primary distinction between the second embodiment of the clip 138 and the first embodiment of the clip 38 is that the second embodiment of the clip 138 includes a pair of magnets 170 coupled thereto, as well as attachment arms 141 for securing the foam liner 174 to the clip 138. The basic structural attributes of the second embodiment of the clip 138 are similar to the basic structural attributes of the first embodiment of the clip 38. In particular, the clip 138 includes a first clip member 142 and a second clip member 144 pivotally connected to the first clip member 142 via a hinge 145. The first and second clip members 142, 144 form opposing locking tabs defining a clip channel 146 (see FIG. 14) therebetween, wherein the clip channel 146 is sized and adapted to receive a portion of the goggle frame 20 to allow the clip 138 to clamp onto the frame 20. The clip 138 further includes a locking arm 156 which operates in a manner similar to the locking arm 56 of the clip 38.

As noted above, the clip 138 includes a pair of attachment arms 141 extending laterally outward from the first clip member 142. The attachment arms 141 are adapted to extend through corresponding openings 143 formed in the foam liner 174 to secure the foam liner 174 to the clip 138. In this respect, the clip 138 and liner 174 are configured to enable selective removal of the liner 174 from the clip. As such, liners 174 with different thicknesses may be used to accommodate different types of foam liners on different goggles.

Two magnets 170 are connected to the clip 138 to enhance the magnetic attraction, compared to just a single magnet. The magnets 170 may be arranged in a side-by-side configuration, wherein the magnetic poles of the magnets 170 are opposite to each other. The external engagement surfaces of the magnets 70 may be slightly offset from each other to define a generally concave configuration to enhance engagement with a corresponding "domed" or arcuately shaped metallic nasal elements.

Figure 15:
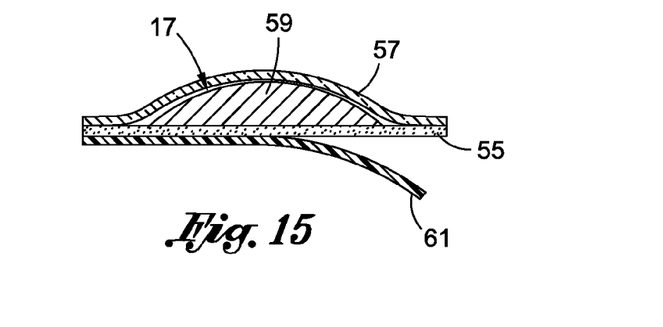
FIG. 15 is a side sectional view of a nose element having a peel-away liner partially removed therefrom.
Figure 16:
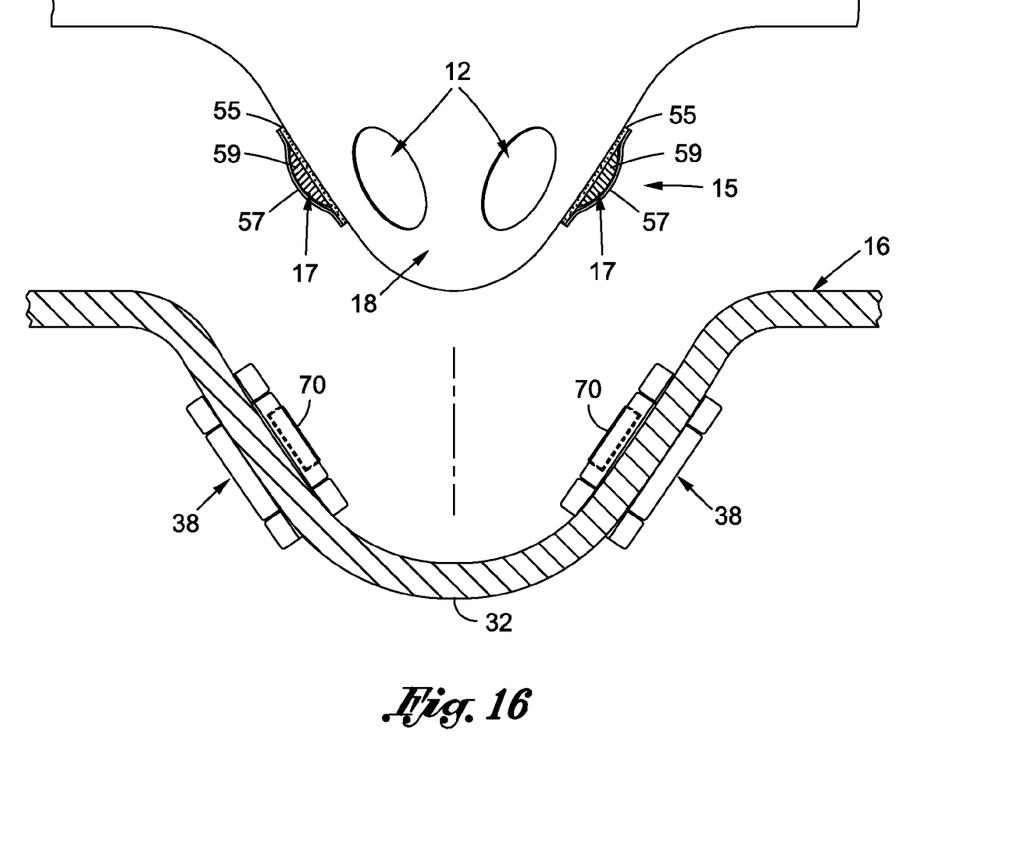
FIG. 16 is a bottom view of the goggle being brought into alignment with the wearer and nasal elements worn by the wearer.

Each nasal element 17 may be secured to the wearer's nose 18 via an adhesive layer 55 located on the underside of the nasal element 17. The use of separate nasal elements 17 allows the user to pinpoint the exact location of each nasal element 17 on the user. Each nasal element 17 may be configured for a one-time use and thus several nasal elements 17 may be packaged and sold as a set. Referring now to FIGS. 15-16, there is depicted a cross sectional view of a nasal element 17, which includes a base layer 55 and an outer layer 57 which collectively encapsulate a magnetically attractable element 59, such as a ferrous material. One or more surfaces of the magnetically attractable element 59 may define an arcuate or "domed" configuration to allow contact between the magnet 70 and the nasal element 17 without flat-to-flat attachment which may create uncomfortable torque on the nostril. The base layer 55 may include a peel-off liner 61 which may be removed to expose adhesive for securing the nasal element 17 to the user's nose 18. The peel-off liner 61 may include a single continuous strip or a segmented strip. The exposed surface of the outer layer 57 may be imprinted with indicia or logos associated with the goggle manufacturer, clip manufacturer, nasal strip manufacturer, sports team, school, the wearer's initials, etc.

Although the foregoing describes the nasal element 17 as being attached to the wearer via an adhesive, it is also contemplated that nasal element 17 may be coupled to the wearer via piercings. It is also contemplated that the nasal element 17 may be coupled to the wearer via a clip which clamps onto the wearer's nose by having one portion that is inserted inside the nostril, and another portion which extends outside the nostril. In this respect, it is understood that any means may be used to attach the nasal element 17 to the wearer to position the nasal element 17 for magnetic coupling to the goggle.

With the basic structural features of one embodiment of the system 10 described above, operation of the system 10 will now be described. Prior to placing the goggles 16 on the wearer's head, the wearer 14 places the nasal attachment members 17 on his nose 18 adjacent the wearer's nostrils (see FIGS. 1 and 16). The nasal elements 17 may have a protective lining covering an adhesive layer, and thus, the wearer 14 may have to peel the protective lining away from each nasal element 17 to expose the adhesive layer. When the adhesive layer is exposed, the wearer presses the nasal element 17 against the wearer's nose 18 to couple the nasal element 17 to the nose 18.

The wearer 14 also attaches the clips 38 to the goggle frame 20 adjacent the bridge section 32 of the frame 20. In particular, the clips 38 are positioned on opposed sides of a bridge apex, such that each clip 38 will be positioned adjacent a respective one of the wearer's nostrils when the goggles 16 are placed on the wearer 14. The clips 38 are attached to the goggle frame 20 from transitioning the clip 38 from the open position toward the closed position, as described in more detail above. When the clips 38 are attached to the goggle frame 20, each clip 38 forms a recess or depression within the foam liner 36 on the goggle 16.

With the nasal attachment members 17 attached to the wearer 14 and the goggle clip 38 attached to the goggles 16, the wearer 14 places the goggles 16 on the wearer's head. Referring now specifically to FIG. 16, as the goggles 16 move toward the wearer's head, the clips 38 move closer to the nasal element 17, thereby causing the magnetic attraction between the clip magnet 70 and the ferrous body 59 to become stronger. When the goggles 16 are placed in their final position, the clip 38 acts as a "perch" or "locator" for the nasal element 17, such that the ferrous body 59 is drawn into magnetic engagement with the clip magnets 70, which in turn causes the nasal passages 12 of the user to dilate. In particular, the nasal attachment members 17 are displaced outward and forward relative to their previous position to dilate the user's nose 18. The dilated nasal passage 12 allows the wearer 14 to breathe easier during physical activity so as to maintain elevated oxygen levels in the body.

Although the foregoing describes the nasal elements 17 and clip 38 as being engageable with magnets 70, it is also contemplated that other connectors may be used to connect the nasal elements 17 to the clip 38 without departing from the spirit and scope of the present invention. For instance, the engagement between the nasal element 17 and the goggle clip 38 may be by way of hook and loop fasteners, magnets, adhesives, or other engagement mechanisms known in the art.

Furthermore, although the embodiment of the clip 38 described above includes separate first and second clip members 42, 44 which are pivotally connected to each other, it is understood that other embodiments of the clip 38 may be used without departing from the spirit and scope of the present invention. Along these lines, the clip 38 may include a single, unitary body having a pair of opposed tabs which are flexible to enable placement of the clip onto the goggle frame 20.

Figure 17:
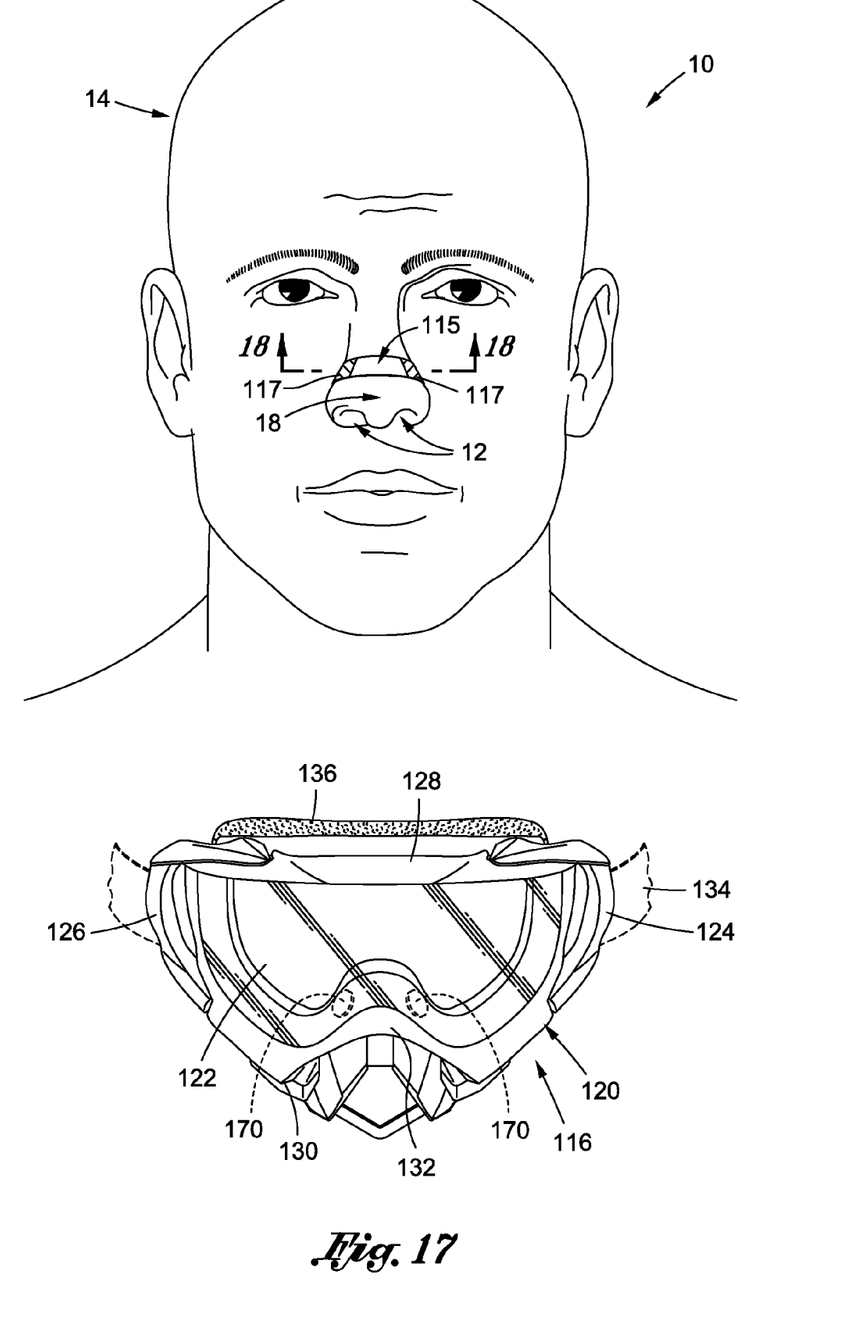
FIG. 17 is a front view of a user wearing a nasal strip and goggles having embedded magnets which urge the nasal strip toward the goggles to open the user's nasal passage when the goggles are worn.
Figure 18:
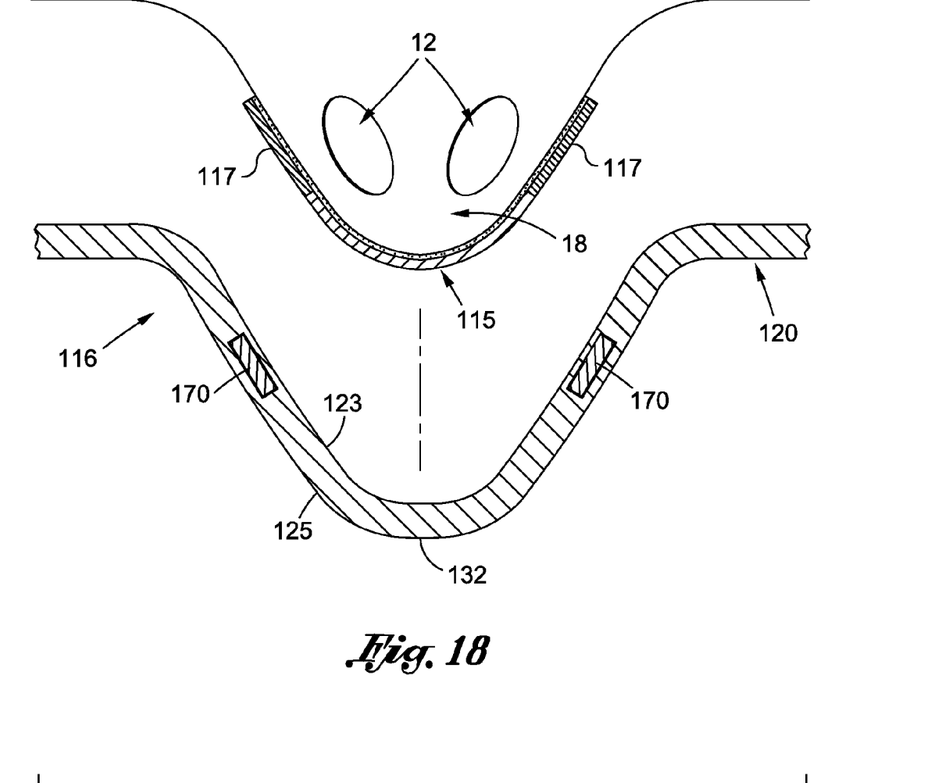
FIG. 18 is a bottom view of the goggles and clips being brought into alignment with the wearer and the nasal strip.
Figure 19:
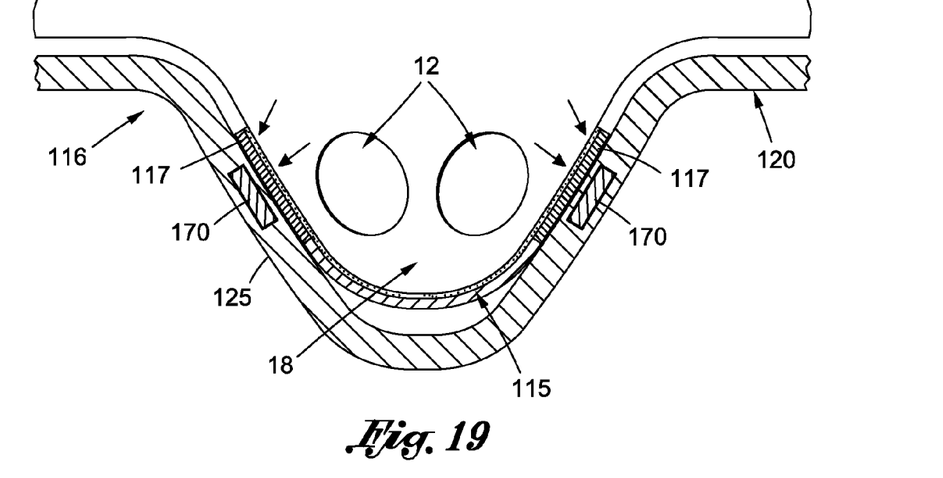
FIG. 19 is a bottom view of the goggles and the clips urging the nasal strip toward the goggle frame to open the wearer's nasal passage.

Referring now to FIGS. 17-19, there is depicted various alternatives to the embodiments described above in relation to FIGS. 1-16. In particular, FIGS. 17-19 show a nasal attachment member 115 including a single nasal strip having a pair of attachment regions 117 on opposed ends of the nasal strip. Each attachment region 117 includes a ferrous body configured to be selectively engageable with a magnet 70 on a corresponding clip 38. The nasal strip 115 preferably includes an adhesive layer to allow the nasal strip 115 to be coupled to the wearer's nose 18.

FIGS. 18 and 19 also show an additional embodiment of a set of goggles 116 having magnets 170 coupled thereto without the use of a separate clip. The goggles 116 include a frame 120 having a frame opening with a lens 122 positioned therein. The frame 120 includes opposed lateral end portions 124, 126, a top portion 128, and an opposing bottom portion 130 having a bridge section 132 which fits over the nose 18 of the wearer 14. A headband or strap 134 may be connected to the opposed lateral end portions 124, 126 of the frame 120 for securing the frame 120 to the wearer's head.

In the embodiment depicted in FIGS. 18 and 19, the magnets 170 are located within the frame 120 between the inner and outer surfaces 123, 125 of the frame 120 and on opposite sides of the bridge apex. The magnets 170 may be embedded within the frame 120, or alternatively, located within a slot formed within the frame 120 to enable removal and replacement of the magnets 170. When the goggles 116 are worn by the wearer 14, the magnets 170 are positioned such that the magnets 170 are magnetically attracted to the magnets in the nasal attachment member 115.

The goggles 116 may be used with various implementations of the nasal attachment member, including a single nasal strip or separate nasal elements. In this respect, although the goggles 116 are specifically shown in FIGS. 18 and 19 as being used with a pair of nasal attachment members 117, it is also contemplated that the goggles 116 may also be used with the nasal strip 15 depicted in FIG. 1.

Those skilled in the art will readily appreciate that although the foregoing discussion describes the magnets as being incorporated in the clip or goggles, and the ferrous body being incorporated into the nasal element or nasal strip, other embodiments may have a reverse configuration, i.e., the magnet is incorporated into the nasal element or nasal strip and the ferrous body is incorporated into the clip or goggle.

It is contemplated that the system 10 may be packaged and sold as a complete set, including goggles, clips and nasal attachment member(s). Alternatively, the clips and nasal attachment member(s) may be sold separately as a set or individually. For instance, the system 10 may be sold as a kit, including two clips, four foam liners for the clips, wherein the foam liners are of two different foam thicknesses, as well as eight nose elements. Of course, other kits may include different numbers of items without departing from the spirit and scope of the present invention.

The particulars shown herein are by way of example only for purposes of illustrative discussion, and are not presented in the cause of providing what is believed to be most useful and readily understood description of the principles and conceptual aspects of the various embodiments of the present disclosure. In this regard, no attempt is made to show any more detail than is necessary for a fundamental understanding of the different features of the various embodiments, the description taken with the drawings making apparent to those skilled in the art how these may be implemented in practice.

What is claimed is:

1. An eyewear system adapted to open a nasal passage of a user having a nose defining the nasal passage, the eyewear system comprising:
   a wearable frame having a bridge section configured to be placeable adjacent the nose of the user;
   a liner coupled to the wearable frame and configured to interface with the user when the wearable frame is placed on the user, the liner being formed from a compressible material;
   a clip configured to be selectively attachable to the wearable frame and adapted to compress the liner when attached to the wearable frame; and
   a nasal attachment member configured to be selectively placeable on the nose of the user adjacent the nasal passage;
   the clip being configured to urge the nasal attachment member toward the wearable frame to cause the nasal passage of the user to open in response to placement of the wearable frame adjacent the nose of the user.

2. The system recited in claim 1, further comprising a peripheral barrier member coupled to the clip and configured to interface with the user to mitigate passage of particulate between the wearable frame and the user when the clip is attached to the wearable frame and the wearable frame is placed adjacent the nose of the user.

3. The system recited in claim 1, wherein the clip includes a first clip member and a second clip member pivotally coupled to the first clip member.

4. The system recited in claim 3, wherein the first clip member is pivotable relative to the second clip member between an open position and a closed position, an angle between the first and second clip members decreasing as the first and second clip members pivot from the open position toward the closed position.

5. The system recited in claim 4, wherein the first and second clip members are configured to become locked when the first and second slip members are in the closed position.

6. The system recited in claim 1, wherein the nasal attachment member is configured to be magnetically urged toward the clip.

7. The system recited in claim 1, further comprising a magnet coupled to the clip and a ferrous body coupled to the nasal attachment member and magnetically attractable to the magnet.

8. The system recited in claim 1, wherein the nasal attachment member includes a nasal strip configured to extend between both nostrils of the user.

9. The system recited in claim 1, wherein the nasal attachment member includes a pair of nasal elements disposable adjacent respective ones of the nostrils of the user.

10. The system recited in claim 1, wherein the wearable frame is a goggle frame adapted to engage with a goggle lens.

11. An eyewear system adapted to open a nasal passage of a user having a nose defining the nasal passage, the eyewear system comprising:

a wearable frame configured to be placeable adjacent the nose of the user; and a nasal attachment member configured to be selectively placeable on the nose of the user adjacent the nasal passage and separate from the wearable frame, the nasal attachment member being configured to be adhered to the nose of the user when placed thereon;

the nasal attachment member being adapted to be magnetically urged toward the wearable frame in response to placement of the wearable frame adjacent the nose of the user to cause the nasal passage of the user to open.

12. The eyewear system recited in claim 11, wherein the nasal attachment member includes an adhesive layer and a ferrous element coupled to the adhesive layer, the adhesive layer being disposable on nose of the user.

13. The eyewear system recited in claim 12, wherein the nasal attachment member includes an arcuate surface adapted to interface with a magnet.

14. The eyewear system recited in claim 12, further comprising a peel-off liner covering the adhesive layer, the peel-off liner being selectively removable from the adhesive layer to expose the adhesive layer before placement on the nose of the user.

15. The eyewear system recited in claim 11, wherein the wearable frame is a goggle frame.

16. An eyewear system adapted to open a nasal passage of a user having a nose defining the nasal passage, the eyewear system comprising:

an eyewear frame configured to be placeable over eyes of the user; and a nasal attachment member configured to be selectively placeable on the nose of the user separate from the eyewear frame;

the nasal attachment member being adapted to be magnetically urged toward the eyewear frame in response to placement of the wearable frame adjacent the nose of the user to cause the nasal passage of the user to open;

the nasal attachment member being adapted to reside on the nose of the user prior to placement of the eyewear frame over the eyes of the user.

17. The eyewear system recited in claim 16, wherein the nasal attachment member includes an adhesive layer and a ferrous element coupled to the adhesive layer, the adhesive layer being disposable on nose of the user.

18. The eyewear system recited in claim 17, wherein the nasal attachment member includes an arcuate surface adapted to interface with a magnet.

19. The eyewear system recited in claim 17, further comprising a peel-off liner covering the adhesive layer, the peel-off liner being selectively removable from the adhesive layer to expose the adhesive layer before placement on the nose of the user.

20. The eyewear system recited in claim 16, wherein the wearable frame is a goggle frame.

\* \* \* \* \*